US006653504B1

(12) United States Patent
Buononato

(10) Patent No.: US 6,653,504 B1
(45) Date of Patent: Nov. 25, 2003

(54) NON-HYGROSCOPIC SALTS OF ACTIVE INGREDIENTS HAVING THERAPEUTICAL AND/OR NUTRITIONAL ACTIVITIES AND ORALLY ADMINISTRABLE COMPOSITIONS CONTAINING SAME

(75) Inventor: Antonietta Buononato, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 60 days.

(21) Appl. No.: 10/069,925

(22) PCT Filed: Aug. 23, 2000

(86) PCT No.: PCT/IT00/00346

§ 371 (c)(1),
(2), (4) Date: Mar. 1, 2002

(87) PCT Pub. No.: WO01/17948

PCT Pub. Date: Mar. 15, 2001

(30) Foreign Application Priority Data

Sep. 3, 1999 (IT) .......................................... RM99A0550

(51) Int. Cl.⁷ ............................................. C07C 229/22

(52) U.S. Cl. ........................ 562/560; 514/546; 514/554; 560/253; 562/561

(58) Field of Search ................................. 562/560, 561; 560/253; 514/546, 554

(56) References Cited

U.S. PATENT DOCUMENTS 4,883,786 A * 11/1989 Puricelli
5,270,472 A * 12/1993 Taglialatela
6,080,786 A * 6/2000 Santaniello

FOREIGN PATENT DOCUMENTS

EP 0 354 848 A 2/1990
WO 98 47857 A 10/1998

* cited by examiner

*Primary Examiner*—Michael L. Shippen
(74) *Attorney, Agent, or Firm*—Nixon & Vanderhye P.C.

(57) ABSTRACT

Derivatives of active ingredients with creatine and ornithine are disclosed having enhanced nutritional and/or therapeutic effects which favorably lend themselves to the preparation of orally administrable solid compositions.

20 Claims, No Drawings

NON-HYGROSCOPIC SALTS OF ACTIVE INGREDIENTS HAVING THERAPEUTICAL AND/OR NUTRITIONAL ACTIVITIES AND ORALLY ADMINISTRABLE COMPOSITIONS CONTAINING SAME

This application is the US national phase of international application PCT/IT00/00346 filed Aug. 23, 2000, which designated the US.

The present invention relates to stable, non-hygroscopic salts of L-carnitine and lower alkanoyl L-carnitine endowed with enhanced nutritional and/or therapeutical efficacy with respect to their inner salts congeners and to solid compositions containing such salts, particularly suited to oral administration.

It has long since known that carnitine and its alkanoyl derivatives lend themselves to various therapeutical utilizations such as e.g. in the cardiovascular field for the treatment of acute and chronic myocardial ischaemia, angina pectoris, heart failure and cardiac arrhythmias. Acetyl L-carnitine is used in the neurologic field for the treatment of both central nervous system disturbances and peripheral neuropathies, particularly diabetic peripheral neuropathy. Propionyl L-carnitine is used for the treatment of chronic arteriosclerosis obliterans, particularly in patients showing the symptom of severely disabling intermittent claudication.

On the other hand, a widespread promotion of carnitine and derivatives thereof has rapidly been taking place towards utilizations other than those purely therapeutical, ever though allied to them.

It has, in fact, been widely recognized that in professional athletes as well as in any subject practising sport at amateur level, L-carnitine supplies energy to the skeletal musculature and increases the resistance to prolonged, intense stress, enhancing the performance capability of such individuals.

In addition, L(-)-carnitine or its lower alkanoyl derivatives constitute indispensable nutritional supplements for both vegetarians, whose diets have a low carnitine content as well as a low content of the two amino acids, lysine and methionine (the precursors of the biosynthesis of L(-)-carnitine in the kidneys and liver) and those subjects who have to live on a diet poor in protein for prolonged periods of time.

Consequently, various compositions containing carnitine or derivatives thereof, either as single components or in combinations with further active ingredients, have recently reached the market of the dietary supplements, health foods, energy foods and similar products.

It has long since been known that L(-)-carnitine and its alkanoyl derivatives are extremely hygroscopic and not very stable when they occur as inner sats (or "betaines") as represented by the formula.

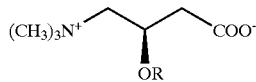

wherein R=H or $C_1$–$C_5$ lower alkanoyl.

This leads to complex problems of processing, stability and storage both of the raw materials and of the finished products. For example, L(-)-carnitine tablets have to be packaged in blisters to keep them out of contact with the air, since, otherwise, even in the presence of normal humidity conditions, they would undergo alterations, swelling up and becoming pasty and sticky.

Since the salts of L(-)-carnitine and its alkanoyl derivatives known to-date present the same therapeutic, nutritional or dietetic activities, respectively, as the so-called inner salts (or "betaines"), the problem of the hygroscopicity of the inner salts has tentatively been solved by salifying them with "pharmacologically acceptable" acids, which do not present unwanted toxic or side effects.

There is now an extensive body of literature, particularly patents, disclosing th e production of such stable, non-hygroscopic salts.

Among L-carnitine salts, particularly L-carnitine tartrate and L-carnitine acid fumarate have to-date found practical utilization.

Although the aforesaid "pharmacologically acceptable" salts solve the problem of the hygroscopicity of L-carnitine inner salt more or less satisfactorily, in none of the known salts the anion moiety co-operates to enhance the nutritional, energetic and/or therapeutical efficacy which can be attributed to the "carnitine" moiety of the salts themselves.

Furthermore, none of the acids used for producing non-hygroscopic L-carnitine salts is capable of forming non-hygroscopic salts of alkanoyl L-carnitine. Thus, for example, whereas L(-)-carnitine acid fumarate and L(-)-carnitine tartrate are non-hygroscopic compounds, acetyl L(-)-carnitine acid fumarate and tartrate, respectively, are strongly hygroscopic compounds, which present the same drawbacks as the corresponding inner salt.

The object of the present invention is to provide stable, non-hygroscopic salts of L-carnitine and lower alkanoyl L-carnitine which possess an enhanced therapeutical and/or nutritional efficacy with respect to the corresponding inner salts.

L-carnitine and alkanoyl L-carnitine choline tartrates are reported to be stable and non-hygroscopic salts in WO 98/47857.

As regards L-carnitine salts with aminoacids, EP-A1-0 354 848 discloses pharmaceutical compositions comprising L-carnitine lysinate as active ingredient, whose preparation and physico-chemical characteristics, however, are not reported. In particular, this reference does not disclose whether the aforesaid L-carnitine lysinate is a hygroscopic or non-hygroscopic substance.

It is, therefore, apparent that the utility of the salts of the present invention is to be found not only in their lack of hygroscopicity and higher stability with respect to their corresponding inner salts, but also insofar as their anion moiety contributes to the nutritional, energetic and/or therapeutic efficacy of the salt as a whole. The aforesaid efficacy of these novel salts is, therefore; not to be attributed exclusively to the "carnitine" moiety of the salt.

The aforesaid object is achieved by the salts of L-carnitine and alkanoyl L-carnitine with creatine and ornithine having the formula (I):

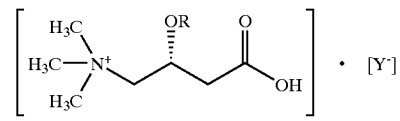

wherein:

R is hydrogen or a straight or branched-chain alkanoyl group having 2–5 carbon atoms; and Y⁻ is selected from:

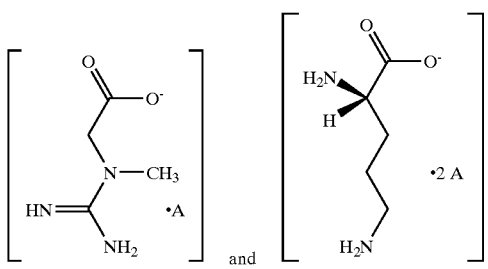

and wherein A is a pharmacologically acceptable acid performing the function of salifying the amino group or groups. Preferably, A is a hydrohalogen acid, such as hydrochloric acid, or phosphoric acid.

When R is alkanoyl, it is preferably selected from the group comprising acetyl, propionyl, butyryl, valeryl and isovaleryl.

Creatine is an organic, nitrogen compound present in considerable amounts in the skeletal muscle tissue of vertebrates wherein about ⅔ thereof occurs as creatine phosphate.

Creatine is biosynthesized mainly in the liver and kidneys from three amino acids: glycine which provides the carbon skeleton, arginine which releases the amidino group and methionine which releases the methyl group. Creatine is excreted with urine as creatinine. Creatine, can be taken with the diet since it is principally present in meat. However, in order to take 10 grams/day of creatine, 2.5 kg of meat should be eaten. The exogenous supply and endogenous biosynthesis must compensate for the daily turn-over of creatine to creatinine which in a 70-kg male subject can be estimated at about two grams.

The physiologic role of creatine is extremely important: principally in the skeletal muscle, but in the brain, liver and kidneys as well, creatine—by reversibly taking up ATP's phosphate groups—plays the role of reservoir of the energy-rich phosphate radicals. This reaction is critically important since ATP can not be stored in tissues in excess of a very limited threshold. It is creatine phosphate whose content in tissues is five times as much that of ATP, which provides for phosphate groups supply. Following a moderately wearying physical exertion, the creatine phosphate present in the skeletal muscle decreases in a far relevant amount than ATP does, thus showing that creatine phosphate rephosphorilates ADP as ATP becomes dephospharilated.

When the rate of ATP's metabolic production exceeds ATP's utilization, this results in creatine phosphate formation. Creatine phosphate is, therefore, a reservoir of immediately available energy, suitable for counterbalancing energy demands exceeding ATP's synthesis rate in metabolic phosphorylation processes.

Creatine is mainly taken by athletes and sportsmen insofar as it increases the skeletal musculature if its intake is accompanied by lasting physical exertion. Creatine intake results in a lowering of fat while it enhances skeletal muscle. Recent researches have shown that the combined intake of creatine and carbohydrates enhances creatine effects owing to insuline production that is stimulated by simple sugars which likely play a role in creatine exportation to muscle cells.

Ornithine, a non-proteogenic amino acid is a lower homolog of lysine and an important intermediate in urea biosynthesis cycle wherein it is synthesized by arginine transguanidinization. Ornithine can also be converted to glutamic acid.

It is, therefore, apparent the advantage of having at one's disposal novel carnitine salts which, in addition of being stable and withstanding environments of high relative humidity (60–70%), combine the therapeutical, nutritional and energizing properties of both L-carnitine or its alkanoyl derivatives and creatine or ornithine.

The following non-limiting examples illustrate the preparation and physico-chemical characteristics of some of the compounds of this invention.

EXAMPLE 1

L-carnitine creatinate phosphate (BS/210)

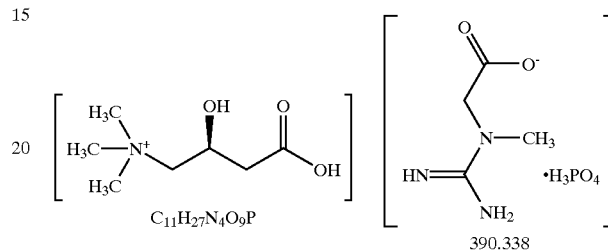

16.1 g (0.1 moles) of L-carnitine inner salt were dissolved in 200 mL of water. To the resulting solution, 13.1 g (0.1 moles) and 7.5 mL of 85% phosphoric acid (0.1 moles) were added. Following complete dissolution, isobutanol was added and the resulting mixture was concentrated under vacuum at 40° C. The residue thus obtained was taken up with acetone and left under stirring for a few hours. The reaction product was crumbled and filtered under vacuum.

The solid thus obtained was washed with acetone and dried in a thermostatic oven at 30° C. overnight. 33.2 g of the title compound were obtained as a white, crystalline, non-hygroscopic solid.

| | |
|---|---|
| Yield | 95% |
| m.p. | 150° C. (dec.) |
| K.F. | = 0.6% |
| [α]20$_D$ | = −15.1 (C = 1% H$_2$O) |
| pH | 3.2 (C = 0.5% H$_2$O) |

| Elementary analysis: | C% | H% | N% | Cl% |
|---|---|---|---|---|
| Calculated: | 42.10 | 7.34 | 15.10 | 9.56 |
| Found: | 42.23 | 7.63 | 15.62 | 9.32 |

NMR: D$_2$O δ=5.5–5.4 (1H,m —CH—); 3.9 (2H, C<u>H</u>$_2$—N—CH$_3$); 3.8–3.5 (2H,m, N—C<u>H</u>$_2$); 3.1 (9H,s, N—(CH$_3$)$_3$); 2.9 (3H,s, N—C<u>H</u>$_3$); 2.7–2.5 (2H,m, —C<u>H</u>$_2$—COOH); 2 (3H,s, COC<u>H</u>$_3$).

| HPLC: | |
|---|---|
| Column: | Hypersil APS-2 (5 μm) 200 × 4.6 |
| Temperature: | = 30° C. |
| Mobile phase: | CH$_3$CN/H$_2$O + 0.05M KH$_2$PO$_4$/CH$_3$CN (65-35 v/v) |
| pH: | 4.7 with H$_3$PO$_4$ |
| Flow-rate | 0.7 mL/min |
| Acetyl-L-carnitine | R$_t$ = 8.5 |
| Creatine: | R$_t$ = 7.4 |

EXAMPLE 2

Acetyl L-carnitine creatinate hydrochloride (BS/211).

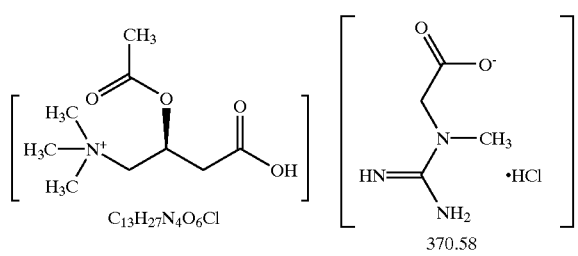

23.9 g (0.1 moles) of acetyl L-carnitine chloride were dissolved in 300 mL of distilled water and to the resulting solution 13.1 g (0.1 moles) of creatine were added under stirring. Following complete dissolution. 300 mL of isobutanol were added and the resulting mixture was concentrated under vacuum at 40° C. The residue thus obtained was taken up with acetone and the mixture kept under stirring. After two hours, the mixture was filtered under vacuum while adding acetone thereto and the residue dried under vacuum in a thermostatic oven at 30° C. overnight. 34 g of the title compound were obtained as a white, crystalline, non-hygroscopic solid.

| | |
|---|---|
| Yield | 96%. |
| m.p. | 161° C. (dec.) |
| K.F. | = 1.6% |
| $[\alpha]20_D$ | = −12.8 (C = 1% $H_2O$) |
| p.H | 3.4 (C = 0.5% $H_2O$) |

| Elementary analysis: | C% | H% | N% | P% |
|---|---|---|---|---|
| Calculated: | 33.84 | 6.97 | 14.35 | 7.94 |
| Found: | 33.58 | 7.07 | 14.25 | 7.81 |

NMR: $D_2O$ δ=4.6–4.5 (1H,m —CH—); 3.9 (2H, C$\underline{H}_2$—N—C$\underline{H}_3$); 3.5–3.4 (2H,m, N—C$\underline{H}_2$); 3.1 (9H,s, N—(CH$_3$)$_3$); 2.9 (3H,s, N—C$\underline{H}_3$); 2.6–2.5 (2H,d, —C$_2$—COOH).

| HPLC: | |
|---|---|
| Column: | Hypersil APS-2 (5 μm) 200 × 4.6 |
| Temperature: | = 30° C. |
| Mobile phase: | $CH_3CN/H_2O$ + 0.05M $KH_2PO_4/CH_3CN$ (65-35 v/v) |
| pH: | 4.7 with $H_3PO_4$ |
| Flow-rate: | 0.7 mL/min |
| L-carnitine: | $R_t$ = 10.1 |
| Creatine: | $R_t$ = 7.4 |

EXAMPLE 3

Acetyl L-carnitine L-ornithate dihydrochloride (BS/212).

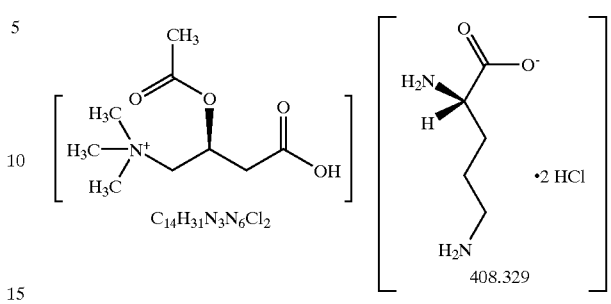

20.3 g (0.1 moles) of acetyl L-carnitine inner salt were dissolved in 100 mL of distilled water and to the resulting solution 20.5 g (0.1 moles) of L-ornithine dihydrochloride were added under stirring.

Following complete dissolution, the mixture was concentrated under vacuum at 40° C. in a rotary evaporator equipped with a water pump at 25 mm/Hg. Isobutanol was added to the concentrate and the resulting mixture was azeotropically distilled. The residue thus obtained was taken up with acetone and kept under mechanical stirring overnight. The mixture was distilled under vacuum with a Gooch filter, no4.

The solid thus obtained was dried under vacuum in a thermostatic oven at 30° C. overnight.

38 g of the title compound were obtained as a white, crystalline, non-hygroscopic solid.

| | |
|---|---|
| Yield: | 96% |
| K.F: | = 0.5 |
| [α 20$_D$ | = −5.7 (C = 1% $H_2O$) |
| pH | 3.2 (C = 1% $H_2O$) |

| Elementary analysis: | C% | H% | N% | Cl% |
|---|---|---|---|---|
| Calculated: | 41.18 | 7.68 | 10.29 | 17.3 |
| Found: | 41.27 | 8.01 | 10.33 | 17.1 |

NMR: $D_2O$ δ=5.5–5.4 (1H,m —CH—); 3.8–3.5 (2H,m, N—C$\underline{H}_2$); 3.7–3.6 (1H, t, C$\underline{H}_2$NH$_2$); 3.1 (9H,s, N—(CH$_3$)$_3$); 3–2.9 (3H, t, N—C$\underline{H}_2$—NH$_2$); 2.7–2.5 (2H,m, —C$\underline{H}_2$—COOH); 2(3H,s, CO—C$\underline{H}_3$); 1.9–1.8 (2H,q, CH$_2$—CH); 1.7–1.5 (2H,m, CH$_2$—C$\underline{H}_2$—CH$_2$).

| HPLC: | |
|---|---|
| Column: | Hypersil APS-2 (5 μm) 200 × 4.6 |
| Temperature: | = 30° C. |
| Mobile phase: | $CH_3CN/H_2O$ + 0.05M $KH_2PO_4/CH_3CN$ (65-35 v/v) |
| pH: | 4.7 with $H_3PO_4$ |
| Flow-rate: | 0.7 mL/min |
| Acetyl-L-carnitine: | $R_t$ = 8.5 |
| Ornithine: | $R_t$ = 12,58 |

In the following Table 1 the increase in weight (%) and appearance of some compounds of the present invention are shown in comparison with the inner salts of L-carnitine and acetyl L-carnitine and the chloride of acetyl L-carnitine following exposure of the compounds to 70±5% relative humidity, at 25° C. for 24 hours.

TABLE 1

| Compound | Increase in weight (%) | Appearance |
| --- | --- | --- |
| L-carnitine inner salt | 23 | deliquescent |
| Acetyl-L-carnitine chloride | 8 | clumped mass |
| Acetyl-L-carnitine inner salt | 19 | deliquescent |
| Example 1 (BS/210) | 0.25 | no variation |
| Example 2 (BS/211) | 0.19 | no variation |
| Example 3 (BS/212) | 0.21 | no variation |

In addition to the advantages of technological nature due to stability and lack of hygroscopicity, the salts of formula (I) present the further advantage for the consumer to make it easy the intake of a proper dose of the active ingredients, which can be easily adjusted to suit the personal needs of a specific individual. The consumer compliance is thus greatly facilitated both in the therapeutic and dietetic field, such as e.g. in training diets, in the nourishment of debilitated and stressed individuals and in vegetarian diets.

What is claimed is:

1. A salt of L-carnitine or alkanoyl L-carnitine with creatine or ornithine having the formula:

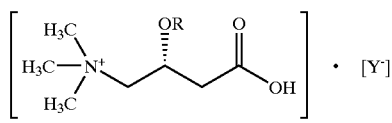

wherein:
R is hydrogen or a straight or branched-chain alkanoyl group having 2–5 carbon atoms; and
$Y^-$ is selected from:

and wherein A is a pharmacologically acceptable acid performing the function of salifying the amino group or groups of creatine or, respectively, ornithine.

2. The salt of claim 1, wherein A is an inorganic acid selected from the group comprising hydrochloric, hydrobromic and phosphoric acid.

3. The salt of claim 1, wherein R is an alkanoyl selected from the group comprising acetyl, propionyl, butyryl, valeryl and isovaleryl.

4. L-carnitine creatinate phosphate.

5. L-carnitine creatinate hydrochloride.

6. Acetyl L-carnitine creatinate phosphate.

7. Acetyl L-carnitine creatinate hydrochloride.

8. L-carnitine L-ornithate dihydrochloride.

9. Acetyl L-carnitine L-ornithate dihydrochloride.

10. Propionyl L-carnitine creatinate phosphate.

11. Propionyl L-carnitine creatinate hydrochloride.

12. Propionyl L-carnitine L-ornithate dihydrochloride.

13. Propionyl L-carnitine L-ornithate dihydrobromide.

14. Isovaleryl L-carnitine creatinate phosphate.

15. Isovaleryl L-carnitine L-ornithate dihydrochloride.

16. A composition comprising the salt of claim 1 and a pharmacologically acceptable excipient and/or diluent therefor.

17. The composition of claim 16 which further comprises vitamins, coenzymes, mineral substances and antioxidants.

18. The composition of claim 16, orally administrable, in the form of a dietary supplement or energizer.

19. The dietary supplement or energizer of claim 18, in the form of lozenges, tablets, pills, capsules, granulates, sachets, syrups or vials.

20. The dietary supplement or energizer of claim 18, in unit dosage form, comprising from about 100 to about 1,000 mg of at least one of the salts.

* * * * *